(12) United States Patent
Hayzlett et al.

(10) Patent No.: US 10,537,349 B1
(45) Date of Patent: Jan. 21, 2020

(54) METHOD FOR PROCESSING TISSUE TO CONTROL THICKNESS

(71) Applicant: LifeCell Corporation, Branchburg, NJ (US)

(72) Inventors: Mark Hayzlett, Flemington, NJ (US); Israel Jessop, Annandale, NJ (US)

(73) Assignee: LifeCell Corporation, Madison, NJ (US)

( * ) Notice: Subject to any disclaimer, the term of this patent is extended or adjusted under 35 U.S.C. 154(b) by 369 days.

(21) Appl. No.: 15/414,804

(22) Filed: Jan. 25, 2017

Related U.S. Application Data

(60) Provisional application No. 62/292,454, filed on Feb. 8, 2016.

(51) Int. Cl.
*A61B 17/32* (2006.01)
*A61B 17/322* (2006.01)

(52) U.S. Cl.
CPC ...... *A61B 17/32* (2013.01); *A61B 2017/3225* (2013.01)

(58) Field of Classification Search
CPC ..................................................... A61B 17/32
USPC ........................................................ 436/174
See application file for complete search history.

(56) References Cited

U.S. PATENT DOCUMENTS

| | | | |
|---|---|---|---|
| 3,023,560 A | 3/1962 | Krahn | |
| 3,076,461 A * | 2/1963 | Parker | A61B 17/322 606/132 |
| 3,076,462 A * | 2/1963 | Parker | A61B 17/322 452/143 |
| 3,324,915 A | 6/1967 | Townsend | |
| 3,515,618 A | 6/1970 | Sidles | |
| 3,631,693 A * | 1/1972 | Morletto | C14B 1/14 69/10 |
| 3,640,279 A * | 2/1972 | Brown | A61B 17/322 606/132 |
| 3,659,639 A * | 5/1972 | Lindstrom | A22C 17/12 99/589 |
| 3,667,521 A * | 6/1972 | Beasley | A22C 17/12 452/127 |
| 3,872,759 A | 3/1975 | Jackson | |
| 4,184,472 A | 1/1980 | Benedicto et al. | |
| 4,253,318 A * | 3/1981 | Repetto | C14B 1/06 69/13 |
| 4,773,418 A * | 9/1988 | Hettich | A61B 17/322 606/132 |
| 5,004,468 A * | 4/1991 | Atkinson | A61B 17/322 606/132 |
| 6,063,094 A * | 5/2000 | Rosenberg | A61B 17/322 606/132 |
| 6,203,540 B1 | 3/2001 | Weber | |

(Continued)

FOREIGN PATENT DOCUMENTS

CN 2125374 U 12/1992
DE 9403937 U1 8/1994
(Continued)

*Primary Examiner* — Arlen Soderquist
(74) *Attorney, Agent, or Firm* — McCarter & English, LLP

(57) ABSTRACT

Devices and methods for processing animal or human tissue are provided. The devices may include a rod having a central axis and configured to simultaneously rotate around the central axis and move along the central axis. The device can further include a group of blades which are attached to the rod and positioned proximate the rigid support surface.

9 Claims, 3 Drawing Sheets

(56) References Cited

U.S. PATENT DOCUMENTS

| | | | |
|---|---|---|---|
| 6,440,143 B2* | 8/2002 | Kasten | A61B 17/322 30/375 |
| 6,685,657 B2 | 2/2004 | Jones | |
| 6,955,110 B1* | 10/2005 | Spletzer | A22C 17/0006 241/260.1 |
| 7,673,545 B1* | 3/2010 | Giberson | B26D 7/02 83/165 |
| 7,682,227 B1* | 3/2010 | Bifulco | A22C 17/0006 452/141 |
| 8,307,762 B1* | 11/2012 | BiFulco | A22C 17/0033 452/160 |
| 9,277,933 B1 | 3/2016 | Jessop et al. | |
| 2001/0029380 A1 | 10/2001 | Ysebaert | |
| 2002/0161385 A1 | 10/2002 | Wiener et al. | |
| 2003/0204199 A1 | 10/2003 | Novak et al. | |
| 2004/0175690 A1* | 9/2004 | Mishra | A61B 17/322 435/1.1 |
| 2004/0175820 A1* | 9/2004 | Shigematsu | G01N 1/06 435/287.1 |
| 2004/0230215 A1* | 11/2004 | Eriksson | A61B 17/322 606/180 |
| 2005/0101972 A1* | 5/2005 | Bhatavadekar | A61B 17/322 606/131 |
| 2005/0222652 A1 | 10/2005 | Mori | |
| 2006/0234614 A1* | 10/2006 | Veldkamp | A22B 5/166 452/129 |
| 2007/0219540 A1 | 9/2007 | Masotti et al. | |
| 2008/0110311 A1* | 5/2008 | Stangherlin | B26F 1/3813 83/177 |
| 2009/0138027 A1 | 5/2009 | Lucas et al. | |
| 2009/0314314 A1 | 12/2009 | Klein et al. | |
| 2010/0022919 A1 | 1/2010 | Peterson | |
| 2010/0049178 A1 | 2/2010 | Deem et al. | |
| 2011/0077664 A1* | 3/2011 | Schulz | A61B 17/322 606/132 |
| 2011/0177591 A1 | 7/2011 | Iwatschenko et al. | |
| 2013/0139559 A1* | 6/2013 | Pedersen | C14B 1/02 69/40 |
| 2014/0107668 A1* | 4/2014 | Zolotov | A61B 17/322 606/132 |
| 2014/0234895 A1 | 8/2014 | Morales | |
| 2015/0197030 A1* | 7/2015 | Fry | B26D 3/28 83/24 |
| 2017/0191906 A1* | 7/2017 | Shibata | C12M 21/08 |
| 2018/0177919 A1* | 6/2018 | Jessop | B26D 7/10 |

FOREIGN PATENT DOCUMENTS

| | | |
|---|---|---|
| DE | 29722914 U1 | 2/1998 |
| WO | 2001/32091 A2 | 5/2001 |

* cited by examiner

METHOD FOR PROCESSING TISSUE TO CONTROL THICKNESS

The present application claims priority under 35 USC § 119 to United States Provisional Patent Application No. 62/292,454, filed Feb. 8, 2016, the entire contents of which is incorporated herein by reference in its entirety.

The present disclosure relates to animal or human tissue processing, and more particularly, to a device and methods for processing animal or human tissue to produce a desired or consistent thickness.

Various tissue-derived products are used to regenerate, repair, or otherwise treat diseased or damaged tissues and organs. Such products can include tissue grafts and/or processed tissues (e.g., acellular tissue matrices from skin, intestine, or other tissues, with or without cell seeding). Such products generally have properties determined by the tissue source (i.e., tissue type and animal from which it originated) and the processing parameters used to produce the tissue products.

Since tissue products are often used for surgical applications and/or tissue replacement or augmentation, the products should support tissue growth and regeneration, as desired for the selected implantation site. To accomplish these goals, the processes for obtaining and processing tissues are selected to avoid unacceptable damage or alteration to the tissues. For example, excessive heating during the procedure will damage the tissue. Therefore, processing the tissue at ambient or controlled temperatures is desirable. In addition, it is desirable for the processing and collection methods to be as efficient as possible without unacceptably harming the tissues.

Collection of tissues used to produce tissue products with a desired thickness generally includes separation of various tissue components from one another. For example, in order to collect portions of skin, such as dermis, for production of dermal tissue products, it is necessary to separate the dermis from subcutaneous tissues such as fat to obtain a tissue with a certain thickness with no damage. Control of the thickness and ensuring consistent thickness across an individual sample, and among a group of tissue samples can be challenging.

Accordingly, the present disclosure provides methods and devices for separating tissues from one another, including separating subcutaneous fat or other tissues from dermis to leave a tissue with a desired or consistent thickness.

SUMMARY

According to certain embodiments, a device for processing animal or human tissue is provided. The device can comprise a rigid support surface for holding a tissue sample, the tissue having a top surface and a bottom surface. The device can further include a rod having a central axis and being configured to simultaneously rotate around the central axis and move along the central axis. Further, the device can comprise a group of blades attached to the rod and positioned proximate the rigid support surface and at least one support member that is attached to the rod.

The group of blades can be positioned such that edges of the group of blades are positioned at an angle between 45 and 90 degrees relative to the rigid support surface. A distance of the group of blades relative to a surface of the tissue can be adjustable The central axis of the rod can be parallel or approximately parallel to the support surface. Each blade in the group of the blades has a center point, and the center point of the group of the blades and the central axis of the rod can be in one plane or aligned on a common axis parallel to the rigid support surface. Further, the group of the blades can comprise five blades.

The rod can comprise a group of grooves for attaching the group of the blades. And the rod can rotate at an adjustable rate.

The device can further comprise a spring for attaching the rod to the at least one support member.

The device may further include a guiding member to move the tissue sample relative to the rod.

The device can include at least one second support member attached to the rod.

According to other embodiments, a method for processing animal or human tissue to produce a desired or consistent thickness is provided. The method can comprise selecting a tissue sample, wherein the tissue sample has a top surface and a bottom surface and placing the tissue sample on a rigid support surface. The method can further comprise causing a group of blades attached to a rod and positioned proximate the rigid support surface to simultaneously rotate around a central axis of the rod and move back and forth along the central axis of the rod to remove a portion of the tissue sample to produce a desired tissue thickness.

The method can further comprise providing at least one support member attached to the rod. The support member can have a cylindrical configuration. The method can further comprise providing at least one second support member attached to the rod.

In addition, the method can comprise positioning the group of blades such that edges of the group of the blades have an angle between 45 and 90 degrees relative to the rigid support surface. The method can further comprise adjusting a distance of the group of blades relative to the bottom surface of the tissue sample.

Each blade in the group of the blades can have a center point. The center point of the group of the blades and the central axis of the rod can be in one plane or aligned along a common axis parallel to the rigid support surface.

The method can further comprise a guiding member for moving the tissue sample relative to the rod.

The method can further comprise providing a spring for attaching the rod to the at least one support member.

The method can comprise adjusting the speed of the rod. The rod can comprise a group of grooves for attaching the group of the blades. The group of the blades can comprise 5 blades.

DESCRIPTION OF EXEMPLARY EMBODIMENTS

Reference will now be made in detail to certain exemplary embodiments according to the present disclosure, certain examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless specifically stated otherwise. Furthermore, the use of the term "including", as well as other forms, such as "includes" and "included", is not limiting. Any range described herein will be understood to include the endpoints and all values between the endpoints.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirely for any purpose.

The present disclosure relates to animal or human tissue processing, and more particularly, to a device and methods for processing animal or human tissue to produce a desired or consistent thickness.

Suitable acellular tissue matrix products include acellular dermal materials such as ALLODERM® and STRATTICE™, which are human and porcine acellular dermal materials available from LIFECELL CORPORATION® (Branchburg, N.J.). In order to produce these acellular dermal materials, it is necessary to isolate the dermis from underlying tissues, including subcutaneous fat. Separation of such materials from the skin, however, can be time consuming. In addition, during the separation process it is important that the dermis remains intact and not damaged by the separation process (e.g., thru mechanical, chemical, or thermal damage). Accordingly, the present disclosure provides improved methods of separation animal or human tissues, including methods for controlling the thickness of tissues for further processing into acellular tissue matrices or other products.

The present devices and methods are described for use in separating dermis from other tissues (e.g., adipose) and/or for controlling the thickness of a skin sample (dermal, or dermal plus a surrounding component such as subcutaneous fat and/or transitional dermis). It should be appreciated, however, that the present devices and methods can be used in a similar manner for other tissues, such as connective tissue, fascia, muscle, adipose tissue attached to other tissue types, ligament, tendon, intestine or intestine components, stomach, omentum, peritoneum, bone, cartilage, bladder, liver, cardiac tissue, or other suitable tissues.

Figure 1:
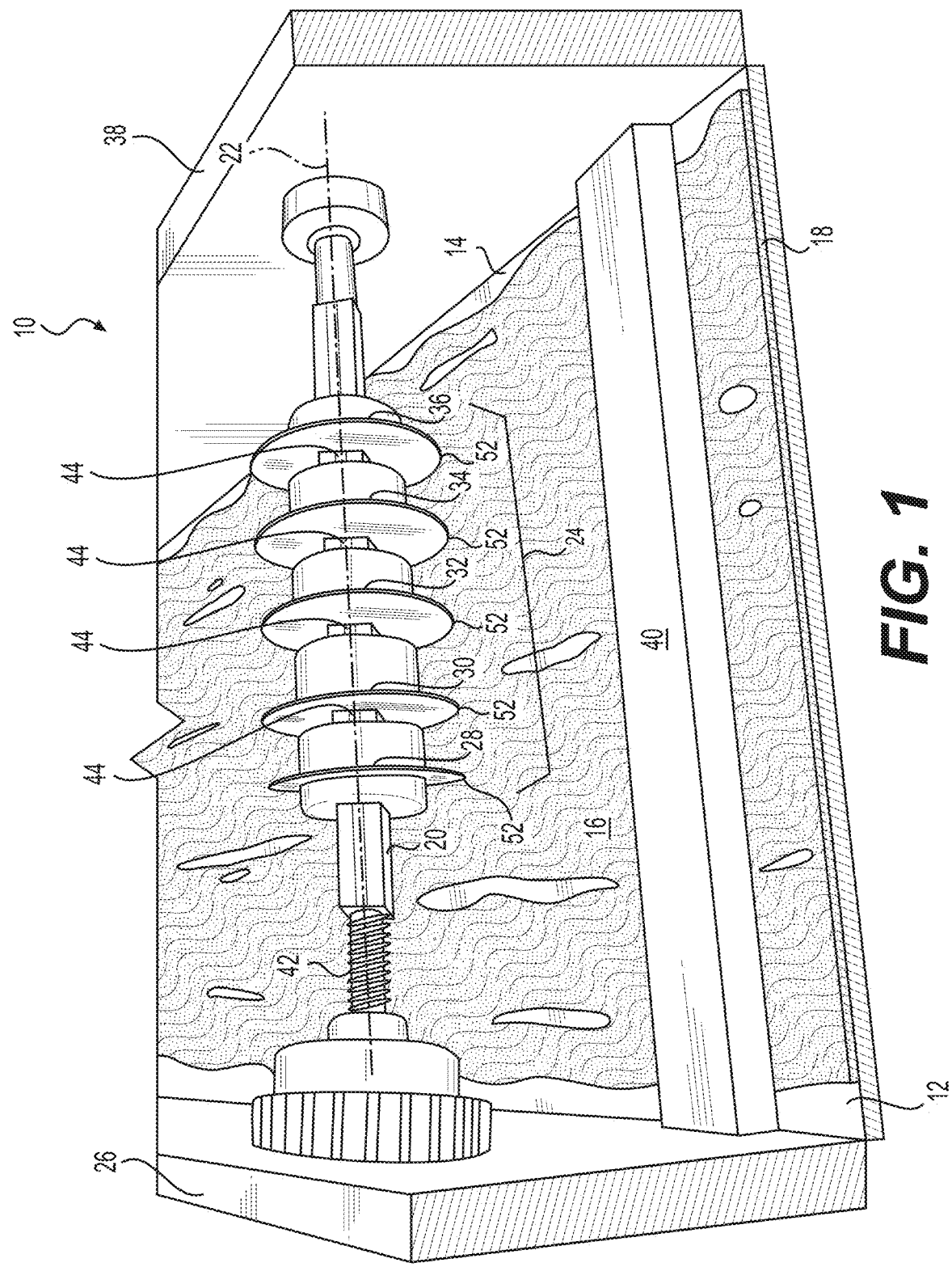
FIG. 1 illustrates a device for processing animal or human tissue, according to certain embodiments.

FIG. 1 illustrates a device 10 for processing animal or human tissue, according to certain embodiments. As shown, the device 10 can comprise a rigid support surface 12 for holding a tissue sample 14, the tissue sample 14 having a top surface 16 and a bottom surface 18 (under the sample or adjacent the support surface).

The device 10 can further comprise a rod 20 having a central axis 22, the rod being configured to simultaneously rotate around the central axis 22 and move along the central axis 22.

Further, the device 10 can comprise a group of blades 24 attached to the rod 20 and positioned proximate the rigid support surface 12. The device 10 can further comprise at least one support member 26 attached to the rod 20.

The rigid support surface 12 can be constructed from a variety of different materials. Generally, the rigid support surface 12 will be substantially or completely flat and constructed from a rigid material such as stainless steel, a rigid plastic, or other similar material. As such, when the section of animal or human tissue 14 is placed on the rigid support surface 12, the section of animal or human tissue 14 will lie flat, and the distance of the group of blades 24 from the rigid support surface 12 will be constant across the area of the tissue sample 14, thereby providing a constant frame of reference for cutting the section of the tissue sample 14.

The rigid support surface 12 can include a variety of shapes and sizes. For example, generally, the rigid support surface 12 will be sized and shaped to allow efficient processing of the selected animal or human tissue. For example, as discussed further below, the tissue sample 14 can include an animal hide (or hide portion) or human donor tissue, including skin and attached subcutaneous tissues, or skin that has been mostly or completely separated from subcutaneous tissues and/or epidermis. In some embodiments, the animal or human tissue comprises porcine skin, and the support surface 12 includes a rectangular shape that is sized for processing typical porcine hides or typically sized human skin samples.

As stated above, the device 10 can include a rod 20. The rod 20 has a central axis 22, and is some embodiments, the central axis 22 of the rod 20 can be positioned parallel to the rigid support surface 12 during operation. The rod 20 can be configured to rotate around the central axis 22 and move back and forth along the central axis 22. The rod 20 can be rotated and/or moved at different speeds, which can be adjusted depending on the tissue sample 14, configuration of blades, or other application-specific factors to obtain a desirable thickness. For example, the rate of rotation and/or movement may affect the smoothness or effectiveness of the sample cutting, and therefore, may be adjusted to optimize or control the precision of the thickness or the desire surface texture (e.g., to produce a very smooth sample or produce a desired roughness).

The rod 20 can be made of a variety of different materials. Generally, the rod 20 will be constructed from a rigid material such as stainless steel, a rigid plastic, metals, or other similar material.

As noted above, the device 10 can include a group of blades 24 attached to the rod 20. In certain embodiments, the device 10 includes between 1 and 200 blades, between 1 and 50 blades, between 1 and 20 blades, between 1 and 10 blades, between 5 and 10 blades, or suitable ranges within. For example, in some embodiments, the group of blades 24 includes a first blade 28, a second blade 30, a third blade 32, a forth blade 34, and a fifth blade 36.

The blades 28, 30, 32, 34, 36 of the group of blades 24 can have a variety of sizes and shapes. Each blade 28, 30, 32, 34, 36 of the group of blades 24 can have different shapes or forms, e.g., each blade 28, 30, 32, 34, 36 can be shaped in a disk form, oval, circular, or any other form. The group of blades 24 can be made of different materials, e.g., stainless steel, metal, alloys, or any similar material.

As shown, the group of blades 24 can be positioned proximate the rigid support surface 12. In addition, the group of blades 24, being attached to the rod 20, can be configured to rotate around the central axis 22 of the rod 20 and/or move back and forth in a direction along the central axis 22 of the rod 20 to separate sections of the tissue sample 14, e.g., to scrape or otherwise cut fat from the tissue sample 14 and/or to reduce the thickness of the sample.

As shown, each blade 28, 30, 32, 34, and 36 in the group of blades 24 has a center point, or in the case of asymmetric blades, an approximate center point. The center point of the group of the blades and the central axis 22 of the rod 20 can be positioned in one plane parallel to or along or near a common axis relative to the rigid support surface 12.

Further, the distance of the lowest edge 52 of the group of blades 24 can be adjusted relative to the bottom surface 18 of the tissue sample 14. For example, the group of blades 24 can be positioned such that the lowest edges 52 of each of the blades 28, 30, 32, 34, and 36 be in contact with the top surface 16 of the tissue sample 14 to remove a certain portion of the tissue sample 14 to produce a desired or consistent thickness. The group of blades 24 can be positioned such that the edges of the group of blades 24 have an angle between 45-90 degrees relative to the rigid support surface 12. Further, the distance between each of the blades of the group of the blades 24 can be adjusted to allow processing of all or a desired portion of the tissue sample 14.

As stated above, the device 10 can comprise at least one support member 26 attached to the rod 20 to secure the rod 20 to the rigid support surface 12; therefore, the rod 20 is securely positioned in place relative to the rigid support surface 12. As shown, the device 10 can further comprise at least one second support member 38 attached to the rod 20 to further support the rod 20 and connect the rod 20 to the rigid support surface 12. The rod 20 can be attached to the at least one support member 26 and the least one second support member 38 in a variety of suitable ways. For example, the rod 20 can be attached to the at least one support member 26 by a spring 42.

As stated above, the group of blades 24 can be attached to the rod 20 in a number of ways. For example, the rod 20 can comprise a group of grooves 44 for attaching each of the blades in the group of blades 24. As a result, each blade in the group of blades 24 can be placed in one groove 44 of the group of grooves 44. Each groove of the group of the grooves 44 can have a width larger than the thicknesses of the blades in the group of the blades 24, but narrow enough to limit movement of the blades 24 to a desired amount. As a result, while the rod 20 moves back and forth along the central axis 22, during operation of the device 10, the blades of the group of the blades 24 will each wobble in the group of the grooves 44, further assisting in removing or scraping a portion of the tissue from the tissue sample 14 to produce a desired or consistent thickness. In some cases, the device is configured to produce low drag on the tissue sample 14 so that the temperature of the tissue sample 14 will be at ambient temperature or controlled to be maintained below a desired temperature during the process, thereby preventing undesirable thermal changes.

The device 10 can further comprise a guiding member 40 to move the tissue sample 14 relative to the rod 20 so that the group of the blades 24 can remove/scrap unwanted tissues from different areas of the tissue sample 14.

Figure 2:
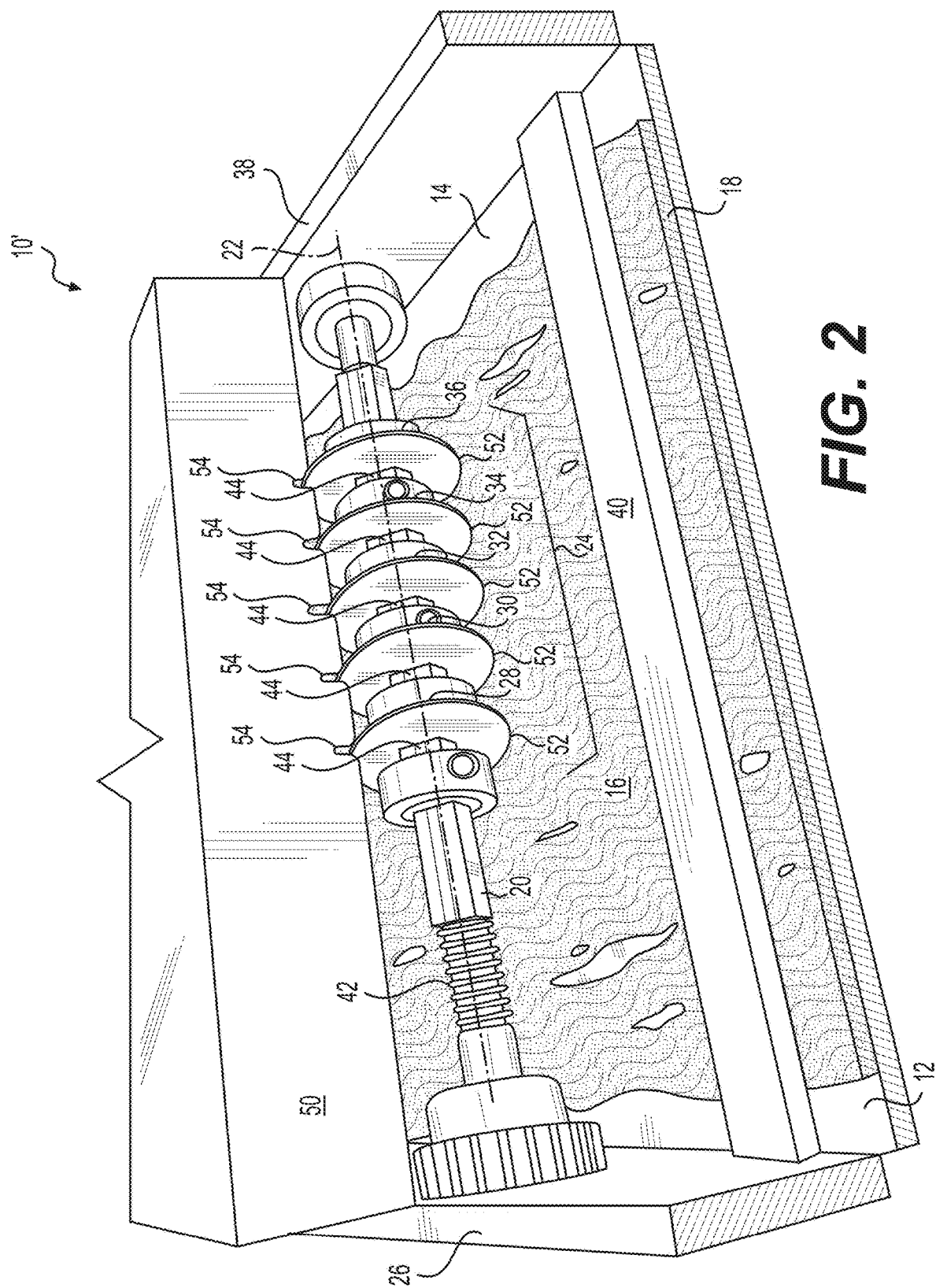
FIG. 2 illustrates a device for processing animal or human tissue, according to certain embodiments.

In some embodiments, the device 10 can include an upper supporting groove member 50 for further securing the group of the blades 24. FIG. 2 illustrates a device 10' for processing animal or human tissue, according to certain embodiments. The groove member 50 can be positioned on top of or above the group of the blades 24. The groove member 50 can include grooves 54 for each blade of the group of the blades 24. Each groove of the groove member 50 can have a width larger than the thicknesses of the blades in the group of the blades 24. In one embodiment the width of the grooves of the groove member 50 have the same width as the grooves in the group of the grooves 44.

The devices 10 and 10' for processing animal or human tissue shown above comprise a rod 20 that includes a group of blades 24. However, a device for processing animal or human tissue can include multiple rods and multiple groups of blades. In order increase processing speed, multiple rods and groups of blades can be incorporated together. Therefore, depending on the size of the tissue to be processed and/or the processing time, multiple rods and blades can be incorporated to the device.

Figure 3:
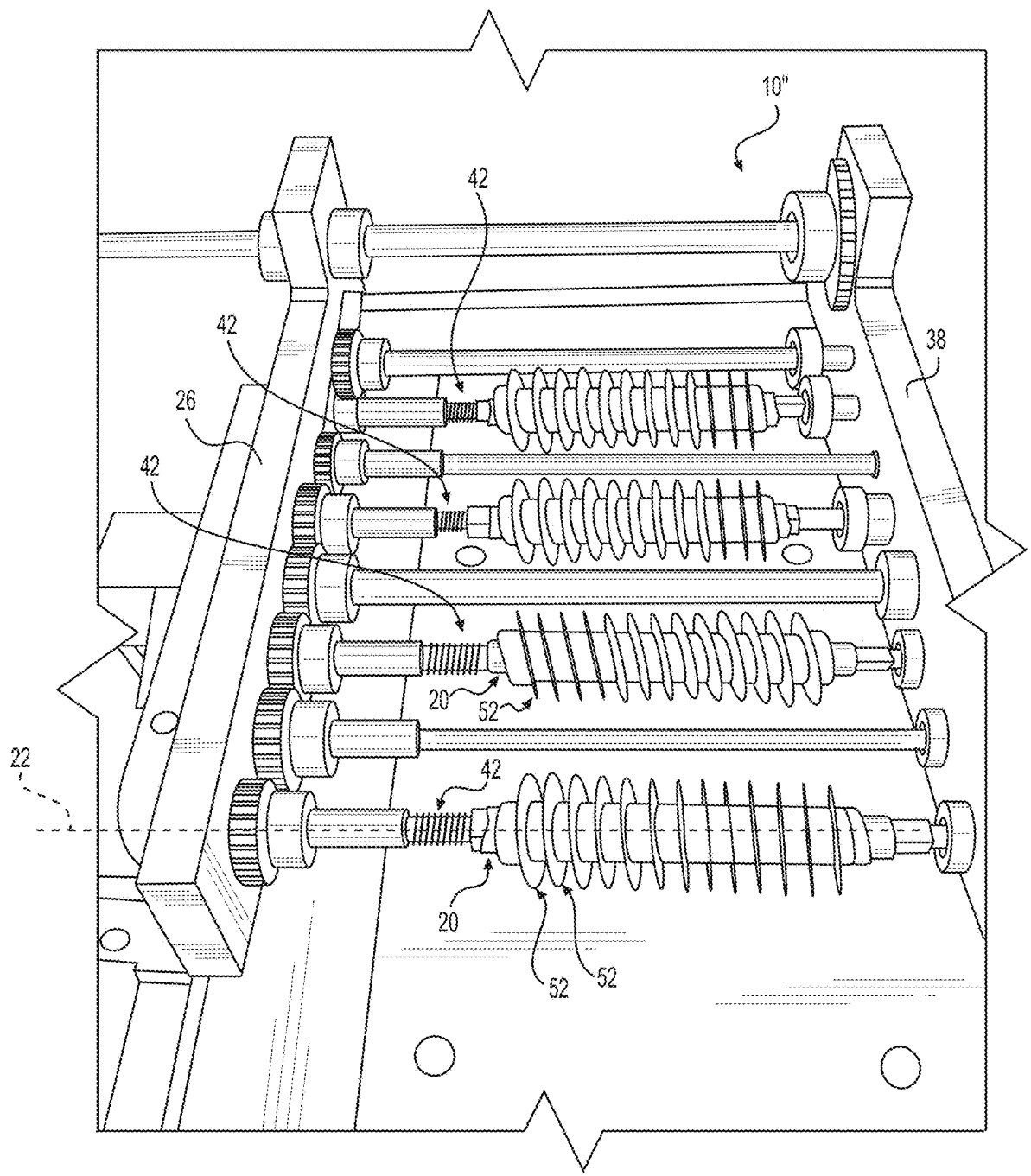
FIG. 3 illustrates a device for processing animal or human tissue, according to certain embodiments.

FIG. 3 illustrates a device 10" for processing animal or human tissue, according to certain embodiments. Device 10" comprises four rods 20 and groups of blades 24. Depending on the size of the tissue sample 14 and the processing time, the number of rods 20 and groups of blades 24 that can be used in device 10" varies. As stated above, if the size of the tissue sample 14 is larger, more rods 20 can be incorporated to process the tissue sample 14.

According to other embodiments, a method for processing animal or human tissue to produce a desired or consistent thickness is provided. The method can comprise selecting a tissue sample 14 having a top surface 16 and a bottom surface 18. The method further comprise placing the tissue sample 14 on a rigid support surface 12. The method can further comprise causing a group of blades 24 attached to a rod 20 and positioned proximate a rigid support surface 12 to simultaneously rotate around a central axis 22 of the rod 20 and move back and/or forth along the central axis 22 of the rod 20 to remove a portion of the tissue sample 14 to produce a desired tissue thickness.

The method can further comprise positioning the group of the blades 24 at an angle such that edges of the group of the blades 24 have an angle between 45 and 90 degrees relative to the rigid support surface 12. In addition, the method can comprise adjusting a distance of the group of blades 24 relative to the bottom surface 18 of the tissue sample 14. The method can further comprise adjusting the speed of the rod 20.

The invention claimed is:

1. A method for processing animal or human dermal tissue to produce a desired thickness comprising:
    selecting a dermal tissue sample, wherein the dermal tissue sample has a top surface and a bottom surface;
    placing the dermal tissue sample on a rigid support surface; and
    causing a group of blades attached to a rod and positioned proximate the rigid support surface to simultaneously rotate around a central axis of the rod and move back and forth along the central axis of the rod to remove a portion of the dermal tissue sample to produce a desired tissue thickness.

2. The method of claim 1, wherein the rod is attached to at least one support member.

3. The method of claim 2, wherein the support member has a cylindrical configuration.

4. The method of claim 1, further comprising positioning the group of blades such that each blade in the group of blades is oriented at an angle of between 45-90 degrees relative to the rigid support surface.

5. The method of claim 1, wherein the central axis of the rod is parallel to the rigid support surface.

6. The method of claim 1, further comprising adjusting a distance of the group of blades relative to the rigid support surface.

7. The method of claim 1, wherein each blade in the group of blades has a center point.

8. The method of claim 7, wherein the center point of the group of blades and the central axis of the rod are in one plane parallel to the rigid support surface.

9. The method of claim 1, further comprising adjusting the speed of the rod.

* * * * *